United States Patent
Adithya et al.

(10) Patent No.: US 10,667,701 B1
(45) Date of Patent: Jun. 2, 2020

(54) SYSTEMS AND METHODS FOR DETERMINING PHYSIOLOGICAL PARAMETERS FROM BLOOD FLOW DYNAMICS

(71) Applicants: Prashanth Chetlur Adithya, Temple Terrace, FL (US); Ravi Sankar, Tampa, FL (US); Wilfrido Alejandro Moreno, Temple Terrace, FL (US); Stuart Hart, Tampa, FL (US)

(72) Inventors: Prashanth Chetlur Adithya, Temple Terrace, FL (US); Ravi Sankar, Tampa, FL (US); Wilfrido Alejandro Moreno, Temple Terrace, FL (US); Stuart Hart, Tampa, FL (US)

(73) Assignee: University of South Florida, Tampa, FL (US)

( * ) Notice: Subject to any disclaimer, the term of this patent is extended or adjusted under 35 U.S.C. 154(b) by 32 days.

(21) Appl. No.: 15/888,889

(22) Filed: Feb. 5, 2018

Related U.S. Application Data (60) Provisional application No. 62/454,507, filed on Feb. 3, 2017.

(51) Int. Cl.
*A61B 5/0205* (2006.01)
*A61B 5/026* (2006.01)
(Continued)

(52) U.S. Cl.
CPC ............ *A61B 5/0205* (2013.01); *A61B 5/026* (2013.01); *A61B 7/023* (2013.01); *A61B 7/04* (2013.01);
(Continued)

(58) Field of Classification Search
CPC ........... A61B 7/04; A61B 7/045; A61B 7/023; A61B 5/02152; A61B 5/021;
(Continued)

(56) References Cited

U.S. PATENT DOCUMENTS 3,565,056 A 2/1968 Statham
4,342,218 A 8/1982 Fox
(Continued)

FOREIGN PATENT DOCUMENTS

IN 201611028804 A * 3/2018

OTHER PUBLICATIONS

S. Romagnoli, Z. Ricci, D. Quattrone, L. Tofani, O. Tujjar, V. Villa, S. Romano and A. Gaudio, "Accuracy of Invasive Arterial Pressure Monitoring in Cardiovascular Patients: An Observational Study," Journal of Critical Care, vol. 18, No. 6, 2014, pp. 644-655.
(Continued)

*Primary Examiner* — John Villecco
(74) *Attorney, Agent, or Firm* — Thomas | Horstemeyer, LLP (57) ABSTRACT

In one embodiment, a system for determining physiological parameters from blood flow dynamics includes a catheter configured for insertion into a blood vessel of a subject through which blood flows, a flexible barrier associated with the catheter configured to oscillate in response to changes in pressure of the blood within the catheter, and a pressure field microphone configured to measure a pressure field induced by the oscillation of the flexible barrier and to generate a measured acoustic pressure signal that can be processed to determine the physiological parameters.

17 Claims, 10 Drawing Sheets

(51) Int. Cl.
| | |
|---|---|
| A61B 7/02 | (2006.01) |
| A61B 7/04 | (2006.01) |
| A61B 5/024 | (2006.01) |
| A61B 5/1455 | (2006.01) |
| A61B 5/08 | (2006.01) |
| A61B 5/0215 | (2006.01) |

(52) U.S. Cl.
CPC ............ *A61B 7/045* (2013.01); *A61B 5/0215* (2013.01); *A61B 5/02444* (2013.01); *A61B 5/0816* (2013.01); *A61B 5/14552* (2013.01); *A61B 2562/0204* (2013.01)

(58) Field of Classification Search
CPC .......... A61B 5/7278; A61B 2562/0204; A61B 5/0205; A61B 5/0215
See application file for complete search history.

(56) References Cited

U.S. PATENT DOCUMENTS

| | | | | |
|---|---|---|---|---|
| 4,383,534 | A * | 5/1983 | Peters | A61B 5/0205 128/207.15 |
| 4,648,406 | A * | 3/1987 | Miller | A61B 5/03 600/487 |
| 5,697,375 | A * | 12/1997 | Hickey | A61B 5/0215 600/486 |
| 6,117,086 | A * | 9/2000 | Shulze | A61B 5/0215 600/486 |
| 6,478,744 | B2 * | 11/2002 | Mohler | A61B 7/04 600/485 |
| 9,504,440 | B2 * | 11/2016 | Hart | A61B 7/04 |
| 9,782,145 | B2 * | 10/2017 | Hart | A61B 7/04 |
| 10,292,660 | B2 * | 5/2019 | Logier | A61B 5/7221 |
| 2002/0102004 | A1 * | 8/2002 | Minervini | B81B 7/0064 381/175 |
| 2003/0220584 | A1 * | 11/2003 | Honeyager | A61B 5/02125 600/559 |
| 2004/0167417 | A1 * | 8/2004 | Schulhauser | A61B 5/0006 600/513 |
| 2004/0249297 | A1 * | 12/2004 | Pfeiffer | A61B 5/02028 600/526 |
| 2007/0287929 | A1 * | 12/2007 | Goedje | A61B 5/02028 600/526 |
| 2008/0013747 | A1 * | 1/2008 | Tran | A61B 7/04 381/67 |
| 2008/0171942 | A1 * | 7/2008 | Brockway | A61B 5/0215 600/486 |
| 2008/0214942 | A1 * | 9/2008 | Oh | A61B 5/02125 600/485 |
| 2008/0234594 | A1 * | 9/2008 | Brooks | A61B 5/0402 600/513 |
| 2010/0030095 | A1 * | 2/2010 | Yu | A61B 7/04 600/526 |
| 2010/0130874 | A1 * | 5/2010 | Joeken | A61B 5/0205 600/485 |
| 2011/0125033 | A1 * | 5/2011 | Saito | A61B 5/021 600/485 |
| 2011/0152628 | A1 * | 6/2011 | Balji | A61B 5/0002 600/300 |
| 2013/0018267 | A1 | 1/2013 | Hart et al. | |
| 2014/0051939 | A1 * | 2/2014 | Messerschmidt | A61B 5/0205 600/301 |
| 2014/0114201 | A1 * | 4/2014 | Watanabe | A61B 5/6898 600/485 |
| 2014/0207062 | A1 * | 7/2014 | Eagle | A61B 5/02141 604/111 |
| 2015/0126880 | A1 * | 5/2015 | Grimbert | A61B 5/0215 600/487 |
| 2016/0051150 | A1 * | 2/2016 | Aarts | A61B 5/021 600/485 |
| 2017/0027458 | A1 * | 2/2017 | Glover | A61B 5/743 |
| 2017/0172537 | A1 * | 6/2017 | Lee | A61B 7/003 |
| 2018/0303354 | A1 * | 10/2018 | Li | A61B 5/0261 |

OTHER PUBLICATIONS

P. Chetlur Adithya, R. Sankar, W. Moreno and S. Hart, "A Novel Acoustic Catheter Stethoscope Based Acquisition and Signal Processing Framework to Extract Multiple Bio Signals," in IEEE Engineering in Medicine and Biology Society, Jeju Island, Korea, 2017, pp. 1336-1339.

P. Chetlur Adithya, S. Pandey, R. Sankar, S. Hart and W. Moreno, "Cluster Analysis Framework for Novel Acoustic Catheter Stethoscope," in NIH—IEEE Special Topics Conference on Healthcare Innovations and Point of Care Technologies: Technology in Translation, Baltimore, MD, 2017, pp. 22-25.

P. Chetlur Adithya, S. Pandey, R. Sankar, W. Moreno, S. Hart and I. Ra, "Bio Acoustic Signal Feature Extraction and Pattern Recognition Framework," in International Conference on Software & Smart Convergence, Vladivostok, Russia, 2017, pp. 1-5.

R. Peura, "Blood Pressure and Sound," in Medical Instrumentation Application and Design, John Wiley & Sons, Inc., 2010, pp. 293-337.

I. Moxham, "Physics of Invasive Blood Pressure Monitoring," Southern African Journal of Anaesthesia and Analgesia, vol. 9, No. 1, 2003, pp. 33-38.

X. Ding, N. Zhao, G. Yang, R. Pettigrew, B. Lo, F. Miao, Y. Li, J. Liu and Y. Zhang, "Continuous Blood Pressure Measurement From Invasive to Unobtrusive: Celebration of 200th Birth Anniversary of Carl Ludwig," IEEE Journal of Biomedical and Health Informatics, vol. 20, No. 6, 2016, pp. 1455-1465.

B. Goldstein, "Intensive Care Unit ECG Monitoring," Cardiac Electrophysiology Review, vol. 1, No. 3, 1997, pp. 308-310.

I. Kerslake and F. Kelly, "Uses of Capnography in the Critical Care Unit," British Journal of Anaesthesia, vol. 17, No. 5, 2016, p. 178-183.

C. Anderson and P. Breen, "Carbon Dioxide Kinetics and Capnography During Critical Care," Critical Care, vol. 4, No. 4, 2000, pp. 207-215.

A. Van de Louw, C. Cracco, C. Cerf, A. Harf, P. Duvaldestin, P. Lemaire and L. Brochard, "Accuracy of Pulse Oximetry in Intensive Care Unit," Intensive Care Medicine, vol. 27, No. 10, 2001, pp. 1606-1613.

J. Allen, "Photoplethysmography and its Application in Clinical Physiological Measurement," Physiological Measurement, vol. 28, No. 3, 2007, pp. 1-39.

J. Lefrant, L. Muller, J. Emmanuel, M. Benbabaali, C. Lebris, N. Zeitoun, C. Mari, G. Saïssi, J. Ripart and J. Eledjam, "Temperature Measurement in Intensive Care Patients: Comparison of Urinary Bladder, Oesophageal, Rectal, Axillary, and Inguinal Methods Versus Pulmonary Artery Core Method," Intensive Care Medicine, vol. 29, No. 3, 2003, pp. 414-418.

Y. Budak, K. Huysal and M. Polat, "Use of a Blood Gas Analyzer and a Laboratory Autoanalyzer in Routine Practice to Measure Electrolytes in Intensive Care Unit Patients," BMC Anesthesiology, 2012, pp. 12-17.

B. Philip and J. Philip, "Characterization of Flow in Intravenous Catheters," IEEE Transactions on Biomedical Engineering, vol. 33, No. 5, 1986, pp. 529-531.

S. Yaniv, U. Zaretsky, P. Halpern and D. Elad, "In Vitro Model of Rapid Intra-Venous Fluid Administration," in IEEE First Joint BMES/EMBS, Atlanta, GA, 1999, p. 237.

I. Chen, Y. Huang and W. Lin, "Flow-Rate Measurements and Models for Colloid and Crystalloid Flows in Central and Peripheral Venous Line Infusion Systems," IEEE Transactions on Biomedical Engineering, vol. 49, No. 12, 2002, pp. 1632-1638.

C. Choi, H. Wu, J. Weyhenmeyer, S. George and B. Cunningham, "Nanodome Sensor Tubing for Monitoring of Intravenous Drug Infusion and Metabolites," in IEEE International Conference on Nanotechnology, Portland, 2011, pp. 161-165.

A. K. Abbas and R. Baseem, Phonocardiography Signal Processing: Synthesis lectures on Biomedical Engineering, Morgan & Claypool Publishers, 2009, 218 pages.

Z. Moussavim, Fundamentals of Respiratory Sounds and Analysis: Fundamentals of Respiratory Sounds and Analysis, Morgan & Claypool Publishers, 2006, 68 pages.

(56) References Cited

OTHER PUBLICATIONS

G.R.A.S. Sound & Vibration, "G.R.A.S. 46AD 1/2" CCP Pressure Standard Microphone Set," G.R.A.S. Sound & Vibration, 2016. [Online]. Available: http://www.gras.dk/46ad.html. [Accessed Jan. 20, 2017], pp. 1-8.

G.R.A.S. Sound & Vibration, "G.R.A.S. 46AE 1/2" CCP Free-field Standard Microphone Set," G.R.A.S. Sound & Vibration, 2016. [Online]. Available: http://www.gras.dk/46ae.html. [Accessed Jan. 20, 2017], pp. 1-9.

National Instruments, "NI 446x Specifications," National Instruments, 2017. [Online]. Available: http://www.ni.com/pdf/manuals/373770j.pdf. [Accessed Jan. 20, 2017], pp. 1-16.

J. Poruba, "Speech Enhancement Based on Nonlinear Spectral Subtraction," in IEEE International Caracas Conference on Devices, Circuits and Systems., Aruba, 2002, pp. 1-4.

R. Udrea and S. Ciochinri, "Speech Enhancement Using Spectral Oversubtraction and Residual Noise Reduction," in International Symposium on Signals, Circuits and Systems, Iasi, Romania, 2003, pp. 165-168.

M. Okazaki, T. Kunimoto and T. Kobayashi, "Multi-Stage Spectral Subtraction for Enhancement of Audio Signals," in IEEE International Conference on Acoustics, Speech, and Signal Processing, Montreal, Canada, 2004, pp. 805-808.

S. Takada, S. Kanba, T. Ogawa, K. Akagiri and T. Kobayashi, "Sound Source Separation Using Null-Beamforming and Spectral Subtraction for Mobile Devices," in IEEE Workshop on Applications of Signal Processing to Audio and Acoustics, New Paltz, NY, Oct. 21-24, 2007, pp. 30-33.

T. Tosanguan, R. Dickinson and E. Drakakis, "Modified Spectral Subtraction for De-noising Heart Sounds: Interference Suppression via Spectral Comparison," in IEEE Biomedical Circuits and Systems Conference, Baltimore, MD, 2008, pp. 29-32.

S. V. Vaseghi, Advanced Signal processing and Digital Noise Reduction: Advanced Digital Signal Processing and Noise Reduction: Second Edition, NY: John Wiley & Sons Ltd., 2000, 493 pages.

S. Haykin, "Frquency—Domain Adaptive Filters," in Adaptive Filter Theory, New Jersey, Prentice Hall, Inc., 1996, pp. 445-478.

K. Hashiodani, T. Onoue, S. Takada, Y. Fukumizu and Y. Yamauchi, "Biosignals Separation Method for Medical Diagnostic System," in 5th International Symposium on Medical Information & Communication Technology (ISMICT), Switzerland, 2011, pp. 156-159.

D. Flores-Tapia, Z. Moussavi and G. Thomas, "Heart Sound Cancellation Based on Multiscale Products and Linear Prediction," IEEE Transaction on Biomedical Engineering, vol. 54, No. 2, Feb. 2007, pp. 234-243.

F. Jin, F. Sattar, S. Razul and D. Goh, "Heart Sound Localization From Respiratory Sound Using a Robust Wavelet Based Approach," in IEEE International Conference on Multimedia and Expo, Hannover, Germany, 2008, pp. 381-384.

J. Welch, P. Ford, R. Teplick and R. Rubsamen, "The Massachusetts General Hospital-Marquette Foundation Hemodynamic and Electrocardiographic Database—Comprehensive collection of critical care waveforms," Journal of Clinical Monitoring, vol. 7, No. 1, Jan. 1991, pp. 96-97.

A. Goldberger, L. Amaral, L. Glass, J. Hausdorff, C. Ivanov P, R. Mark, J. Mietus, G. Moody, C. Peng and H. Stanley, "Components of a New Research Resource for Complex Physiologic Signals," PhysioBank, PhysioToolkit, and PhysioNet, vol. 101, No. 23, Jun. 13, 2000, pp. 1-6.

\* cited by examiner

SYSTEMS AND METHODS FOR DETERMINING PHYSIOLOGICAL PARAMETERS FROM BLOOD FLOW DYNAMICS

CROSS-REFERENCE TO RELATED APPLICATION

This application claims priority to U.S. Provisional Application Ser. No. 62/454,507, filed Feb. 3, 2017, which is hereby incorporated by reference herein in its entirety.

BACKGROUND

Optimizing and improving patient morbidity and mortality outcomes is the primary objective of monitoring in critical and emergency care. Heart rate, respiratory rate, blood pressure (arterial and venous), blood oxygenation, and core temperature are the fundamental cardiovascular hemodynamic parameters that are continuously monitored for patients in critical and emergency care. From a systemic view, critical and emergency care monitoring can be summarized as a two-stage process. At the first stage, multiple sensors acquire vital biological signals corresponding to various physiological processes of the patient. At the second stage, a clinical information system is used to integrate and visualize the data from the multiple sensors used in first stage. State-of-the-art sensing technologies traditionally determine critical parameters from the vital biological signals, i.e., heart rate is determined either from electrocardiogram (ECG) or photoplethysmograph (PPG) using 12-lead electrodes or a fingertip pulse oximetry; respiratory rate is determined either from respiratory flow or respiratory/lung sounds using a plethysmograph or a pneumatograph; continuous blood pressure is determined by coupling the vascular pressures to a intravascular or extravascular pressure sensor through an arterial catheter; blood oxygenation from pulse oximetry, and core body temperature is measured using either a pulmonary arterial catheter or a urinary Foley catheter.

Traditionally, ECG is known for producing the highest quality measurement of heart rate, but it has been shown within the literature that heart rate measured from heart sounds is equally as reliable as ECG. Furthermore, the 12-lead ECG and respiratory data acquisition systems cause patient discomfort and restrict patient mobility. Though pulse oximetry is the gold standard monitoring technology for measuring blood oxygenation, the characteristics of the PPG signal are not fully understood among the medical community and it is still an area of active research. Also, blood oxygenation measurements of PPG are inaccurate when partial pressure levels of oxygen are high, and the inaccuracies also depend on properties of the skin which remain highly subjective. Accomplishing monitoring from the dynamics of the blood flow is currently limited to measurement of continuous blood pressure and core body temperature. Specifically, core body temperature sensing technologies require use of an additional catheter rather than using a preexisting arterial or venous line. Overall, the existing gold standard sensing technologies need multiple assessment systems in order to monitor critical cardiovascular hemodynamic parameters corresponding to various physiological processes. In addition, the existing clinical information systems face limitations to achieve medical device interoperability, as accomplishing the integration and synchronization of various data acquisition systems used in the first stage is complicated. Existing information systems also do not acquire and store high-resolution data. As a result, the complete morphology of the data acquired from various physiological sensors is not currently being used for clinical interventions. In addition, existing systems do not support the application of advanced data processing algorithms and as a consequence, providing real time support for clinical decision making still remains as an unsolved challenge.

From the above discussion, it can be appreciated that it would be desirable to have a system and method that can be used to determine critical physiological parameters without requiring multiple systems that each measures a discrete parameter.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, it can be appreciated that it would be desirable to have a system and method that can be used to determine critical physiological parameters without requiring multiple systems that each measures a discrete parameter. Disclosed herein are systems and methods with which parameters, such as heart rate, respiration rate, and blood pressure, can be determined from a single physiological phenomenon: blood flow dynamics. In one embodiment, a system includes a catheter configured for insertion into a subject's blood vessel, such as an artery or vein. This blood flows into the catheter and is placed in fluid communication with a flexible membrane that transforms the fluctuations in the blood flow into a pressure field that propagates through air contained within a waveguide. A microphone provided within the waveguide senses the acoustic pressure waves as sound signals. After enhancing these signals through noise cancellation, heart sounds and respiratory sounds can be extracted from the signals using signal processing techniques and those sounds can be used to determine heart rate and respiration rate. In addition, signal processing techniques can be used to determine continuous blood pressure from the signals. In some embodiments, the heart sounds and respiratory sounds are extracted using a wavelet-based source separation technique while the continuous blood pressure is determined using a regression model.

In the following disclosure, various specific embodiments are described. It is to be understood that those embodiments are example implementations of the disclosed inventions and that alternative embodiments are possible. All such embodiments are intended to fall within the scope of this disclosure.

System and Data Acquisition

Figure 1:
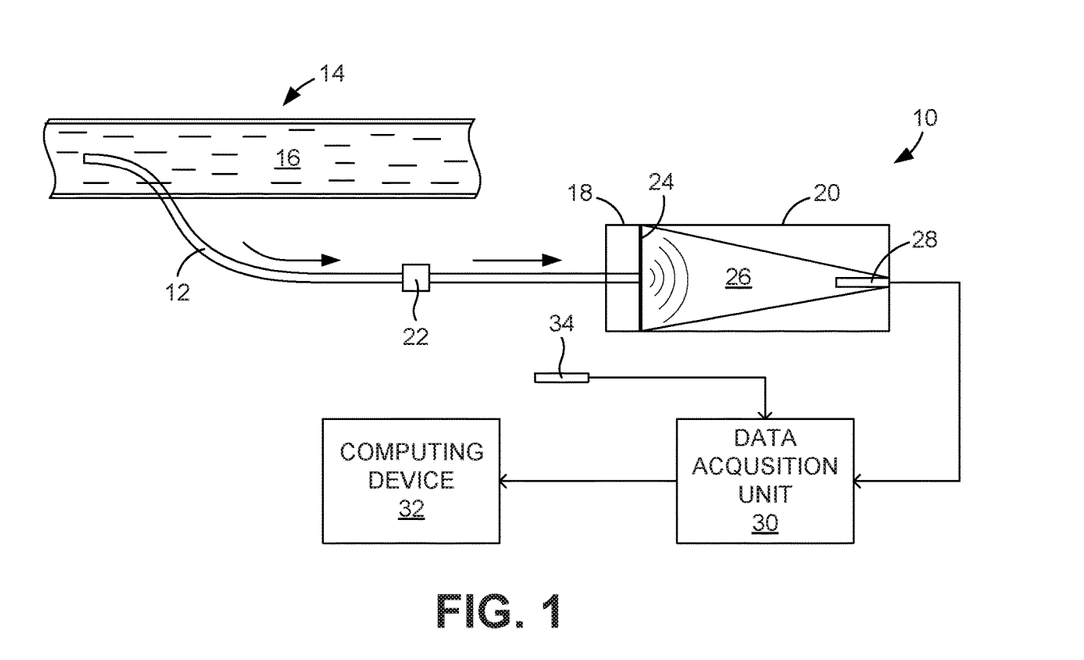
FIG. 1 is a schematic diagram of an embodiment of a system for determining multiple physiological parameters from blood flow dynamics.

FIG. 1 illustrates an embodiment of a system 10 for determining multiple physiological parameters from blood flow. As shown in this figure, the system 10 includes a catheter 12 comprising a flexible tube that is configured for insertion in a subject's blood vessel 14, such as an artery or vein. When so inserted, the distal end of the catheter 12 is immersed in the blood 16 that flows through the vessel 14. The proximal end of the catheter 12 is received by, and therefore connected to, a coupling member 18 that is, in turn, connected to a waveguide 20. In some embodiments, the coupling member 18 is mounted to the waveguide. As is also shown in FIG. 1, a port 22 can be provided along the length of the catheter 12 between its distal and proximal ends. When provided, this port 22 can be used to flush the catheter 12 with an appropriate fluid, such as saline.

Mounted to the coupling member 18 is a flexible barrier 24. This barrier 24 can be formed as a thin polymeric membrane that is on a first side in fluid communication with the blood delivered to the coupling member 18 by the catheter 12 and on a second side in fluid communication with air contained within an interior air chamber 26 of the waveguide 20. Blood flows from the venous or arterial vessel 14 through the catheter 12 and to the barrier 24, which halts the flow of blood and acts as a fluid-to-air coupler. At this boundary, the blood column oscillates due to changes in the stagnation pressure within the catheter, i.e., the frequency at which the blood is being pumped. The stagnation pressure that is impinged onto the barrier 24 induces a pressure field (in the form of pressure waves) that propagates along the air chamber 26 of the waveguide 20 from its distal end, at which the barrier 24 is located, to its proximal end, at which a first microphone 28 is located. By way of example, the first microphone 28 can comprise a condenser microphone, such as the GRAS 46 AD microphone. As shown in FIG. 1, the air chamber 26 can be conical and arranged such that the barrier 24 is located at its wide end and the first microphone 28 is located at its narrow end. In such a case, the acoustic pressure waves are focused on the first microphone 28 for maximal energy transfer.

The pressure field sensed by the first microphone may be designated as the total pressure, $P_{total}$. According to the basic principles of the fluid mechanics, $P_{total}$ is the sum of static pressure, $P_{static}$, and dynamic pressure, $P_{dynamic}$. $P_{static}$ results from intramolecular interaction and $P_{dynamic}$ results from the velocity of the blood flow. It was also observed that the first microphone 28, which may be referred to as a pressure field microphone, partly cancels out the $P_{static}$ data from the acquired total $P_{data}$ through a static pressure equalization vent in the waveguide 20 (not shown) that was originally designed to equalize the effect of ambient pressure. Therefore, it was concluded that the acquired $P_{total}$ predominantly comprises pressure data corresponding to $P_{dynamic}$ with trace amounts of $P_{static}$. As described below, $P_{dynamic}$ can be used to determine heart signals and respiratory signals, while $P_{static}$ can be used to determine continuous blood pressure.

The pressure field sensed by the first microphone 28 is transmitted to a data acquisition unit 30 as an analog acoustic pressure signal. The data acquisition unit converts the analog acoustic pressure signal into a digital acoustic pressure signal that can then be transmitted to a computing device 32 for signal processing. An analog acoustic signal is also provided to the data acquisition unit 30 from a second microphone 34 that is positioned within the environment surrounding the subject for the purpose of collecting ambient noise that, as described below, can be used for noise cancellation purposes. By way of example, the second microphone 34, which may be referred to as an acoustic microphone, can also comprise a condenser microphone, such as the GRAS 46 AE. As with the analog acoustic pressure signal from the first microphone 28, the analog acoustic signal from the second microphone 34 can be digitized by the data acquisition unit 30 and provided to the computing device 32 for signal processing.

Figure 2:
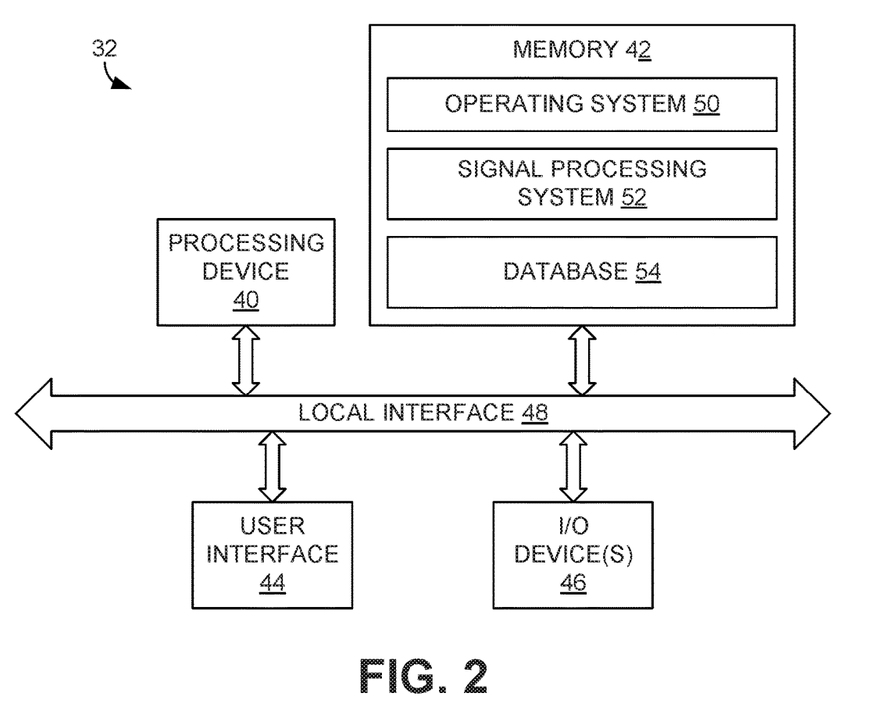
FIG. 2 is a block diagram of an embodiment of a computing device shown in FIG. 1.

FIG. 2 illustrates an example configuration for the computing device 32 shown in FIG. 1. Generally speaking, the computing device 32 can comprise any device that has the computing power to execute software programs necessary to perform the signal processing described below. Accordingly, the computing device 32 can be configured as a desktop computer, a notebook computer, a tablet computer, or a dedicated device configured solely for use in determining physiological parameters from the pressure signals. Irrespective of its configuration, the computing device 32 generally includes a processing device 40, memory 42, one or more user interface devices 44, and one or more input/output devices 46, each of which is connected to a local interface 48.

The memory 42 (a non-transitory computing device-readable medium) of the computing device 32 stores an operating system 50 and a signal processing system 52. The signal processing system 52 comprises one or more software programs, which include one or more algorithms (comprising computer logic and executable instructions), that process the digitized acoustic pressure signals received from the data acquisition unit 30 for the purpose of determining one or more of the physiological parameters. Example physiological parameters include heart rates, respiratory rates, and continuous blood pressure. Examples of operation of the signal processing system 52 in determining such parameters are provided below. As is also shown in FIG. 2, the memory 52 can further include a database 54 in which the received pressure signals and the determined physiological parameters can be stored.

It is noted that experiments were performed using a system similar to the system 10 shown in FIG. 1 as part of a study intended to evaluate the system and the signal processing techniques. In these experiments, vascular pressures were obtained from various arterial and venous body sites of an anesthetized Yorkshire pig in a supine position. A total of 12 pressure measurements were obtained from six different body sites as part of the study. Two different pressure measurements were obtained at each body site, one without the influence of epinephrine and other with influence of epinephrine. Table 1 identifies the sequence in which the experiments were conducted for all the acquired pressure measurements. In addition, heart rate, respiratory rate, and blood pressure were measured using conventional medical devices prior to and after the vascular pressure acquisition for the purpose of benchmarking.

TABLE 1

Design of Experiments for Measured Blood Flow Dynamics

| Index | Body Site | | Catheter Size | Epinephrine |
|---|---|---|---|---|
| 1a | Artery | Carotid | Left Side of Neck | 5F | No |
| 1b | Artery | Carotid | Left Side of Neck | 5F | Yes |
| 2a | Venous | Jugular | Right Side of the Neck | 5F | Yes |
| 2b | Venous | Jugular | Right Side of the Neck | 5F | No |
| 3a | Venous | Femoral | Right Leg | 4F | No |
| 3b | Venous | Femoral | Right Leg | 4F | Yes |
| 4a | Venous | Femoral | Left Leg | 6F | No |
| 4b | Venous | Femoral | Left Leg | 6F | No |
| 5a | Artery | Peripheral | Left Ear | 20F | No |
| 5b | Artery | Peripheral | Left Ear | 20F | Yes |
| 6a | Artery | Femoral | Left Leg | 5F | No |
| 6b | Artery | Femoral | Left Leg | 5F | Yes |

Signal Processing As noted above, once the pressure signals are obtained using the system 10, signal processing techniques can be performed to determine the desired physiological parameters that can be extracted from the signals. A signal processing framework, embodied as the signal processing system 52, was developed for this purpose. The signal processing framework follows a basic approach in the extraction and analysis of $P_{static}$ and $P_{dynamic}$ from $P_{total}$, which is the acoustic pressure signal that is measured by the system 10. Analyzing the acoustic field using a $P_{dynamic}$ processing framework resulted in acoustic heart and respiratory signals. Reconstructing the pressure field using a $P_{static}$ processing framework resulted in continuous blood pressure, i.e., systolic and diastolic pressures.

Figure 3:
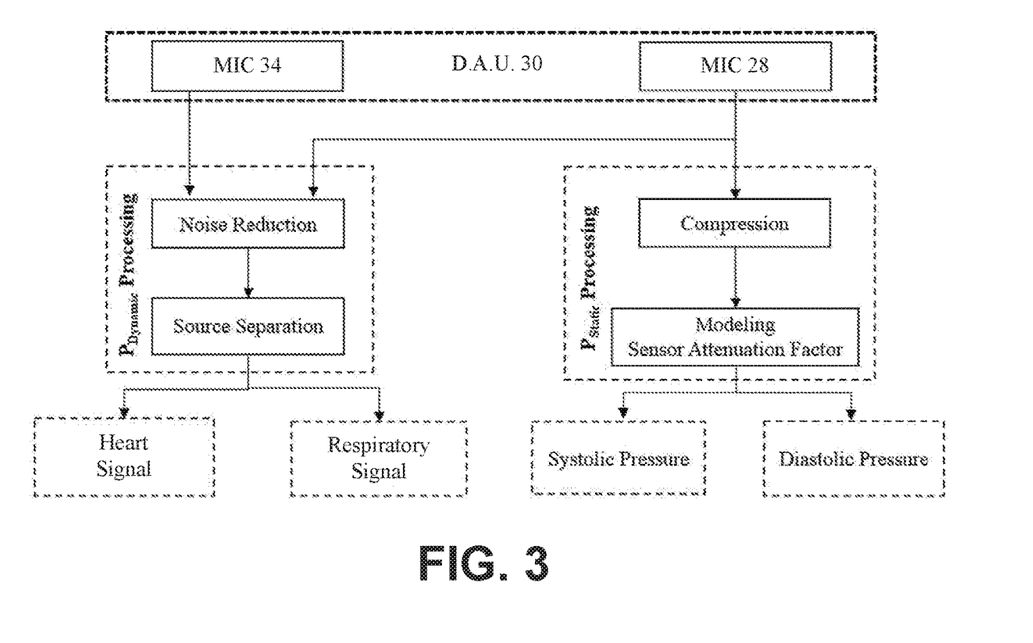
FIG. 3 is a block diagram of an embodiment of a signal processing framework that can be used to extract physiological parameters from the blood flow dynamics.

FIG. 3 is a block diagram that provides an overview of the signal processing framework. As is apparent from this diagram, acoustic biological signals, including an acoustic heart signal and an acoustic respiratory signal, can be extracted by first performing noise cancellation on the acoustic pressure signal (i.e., pressure data) measured by the first microphone with reference to the acoustic signal/data obtained from the second microphone to obtain an enhanced acoustic pressure signal and then performing source separation on the enhanced acoustic pressure signal. In addition, systolic and diastolic blood pressure can be determined by first performing compression on the acoustic pressure signal/data measured by the first microphone and then applying a sensor attenuation factor regression model. Details about these processes are described below.

Acoustic Heart and Respiratory Signal Extraction

Analysis and processing of $P_{dynamic}$ can be viewed as a problem that requires a combination of active noise cancellation and source separation for signal-to-noise ratio (SNR) improvement and biological signal extraction. $P_{dynamic}$ is the result of acoustic pressure created by the oscillation of the blood column at the boundary of the barrier, effectively the sound of the blood flow or the acoustic field of the blood flow. Because the measurement may be made in a noisy clinical setting, the blood flow sounds can be corrupted by other acoustical sources present in the environment. Thus, in order to extract the biological signals with fidelity from this measurement, acquired $P_{dynamic}$ can be enhanced using a noise cancellation technique. A source separation technique based on multiresolution analysis (MRA) was developed in order to extract multiple biological signals from the SNR-enhanced acoustic pressure signal. These processes are illustrated in the flow diagram of FIG. 4, which may be described as a method for extracting acoustic heart and respiratory signals from a measured blood flow acoustic pressure signal.

Figure 4:
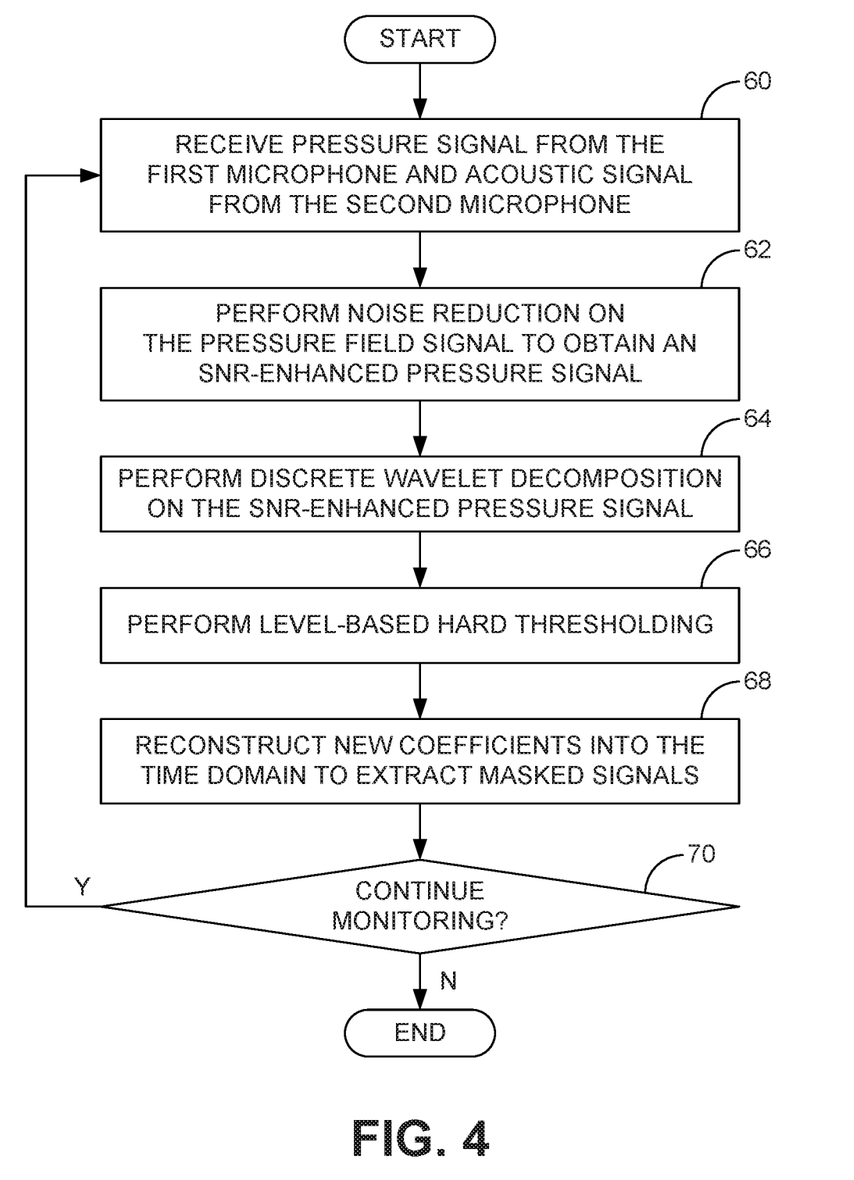
FIG. 4 is a flow diagram of an embodiment of a method for extracting acoustic heart and respiratory signals from a measured blood flow acoustic pressure signal.
Figure 5:
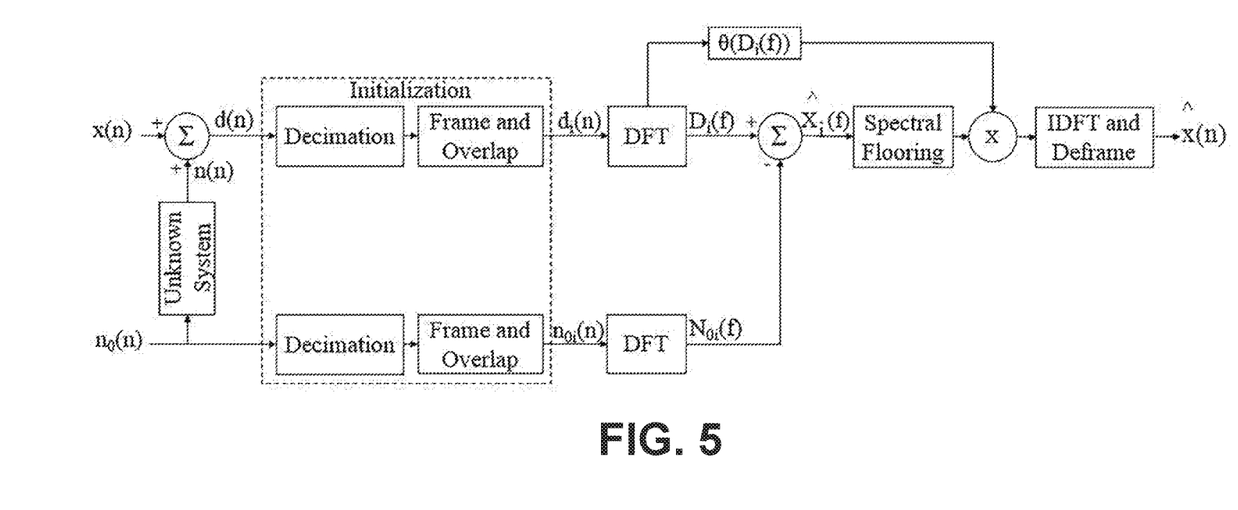
FIG. 5 is a block diagram of an embodiment of a spectral subtraction algorithm.

Beginning with block 60 of FIG. 4, an acoustic pressure signal is received from the first microphone 28 and an acoustic signal is received from the second microphone 34. As noted above, these signals have been digitized by the data acquisition unit 30. Next, with reference to block 62, noise reduction is performed on the acoustic pressure signal to obtain an SNR-enhanced acoustic pressure signal. Spectral subtraction is one noise reduction technique used in applications that require cancellation of interference from acoustic noise. Although studies have used a single channel spectral subtraction technique that assumed stationarity of noise in order to improve the SNR of sound pressure measurement, it has been determined that multichannel spectral subtraction is not only computationally simple but also efficient in improving the SNR of sound pressure measurements, particularly when a part of reference acoustic noise is assumed to be superimposed into the sound pressure measurement by means of an unknown system. The fluid-filled catheter 12 and the waveguide 20 of the system 10 were identified as the major components of the system with unknown impulse responses through which the noise n(n) that is correlated to reference acoustic noise $n_0(n)$ gets superimposed onto the desired signal x(n). A spectral magnitude subtraction technique can be implemented to remove the noise superimposed onto the data channel. FIG. 5 is block diagram of a spectral subtraction algorithm that is suitable for this purpose.

The spectral subtraction algorithm of FIG. 5 includes a data channel that measures the acoustic field of the blood flow dynamics (d(n), where n is the sample index) and a noise channel that measures reference acoustic noise from the clinical setting ($n_0(n)$). The noisy measurement d(n) acquired in the data channel is a result of superimposition of desired signal x(n) and a manifestation of reference acoustic noise n(n). Equation 1 provides time domain model for the noisy measurement.

$$d(n)=x(n)+(n) \quad \text{(Equation 1)}$$

In this equation, d(n) and $n_0(n)$ were passed through an initialization block that decimated the signals from 10 kHz to 1 kHz and then segmented to 2 second long frames with 80% overlap. Each data frame ($d_i(n)$, where i is the frame index) and noise frame ($n_{0i}(n)$) was windowed using a rectangular window and transformed into frequency domain using discrete Fourier transform (DFT). Then, each incoming frequency-transformed data frame ((f)) and noise frame $N_0(f)$ was subjected to magnitude spectral subtraction to provide an estimate of desired signal $|\hat{X}_i(f)|$ as shown in Equation 2.

$$|\hat{X}_i(f)|=|D_i(f)|-|N_{0_i}(f)| \quad \text{(Equation 2)}$$

Equation 2 resulted in processing distortions by producing negative values in the estimated magnitude spectrum owing to the variations of the noise channel spectrum. Hence, the estimated magnitude spectrum $|\hat{X}_i(f)|$ is processed by spectral flooring function to prevent negative values in the estimated magnitude. Equation 3 presents the function that was used to perform spectral flooring.

$$|\hat{X}_i(f)| = \begin{cases} 0.01|D_i(f)| & \text{if } |\hat{X}_i(f)| < 0 \\ |\hat{X}_i(f)| & \text{otherwise} \end{cases} \quad \text{(Equation 3)}$$

The spectral floored magnitude spectrum estimate $|\hat{X}_i(f)|$ is combined with the phase of the noisy signal spectrum $\theta(D_i(f))$ and then transformed into the time domain via inverse DFT (IDFT). Finally, concatenating the outputs from the IDFT yielded an estimate of the desired signal (n).

Figure 6:
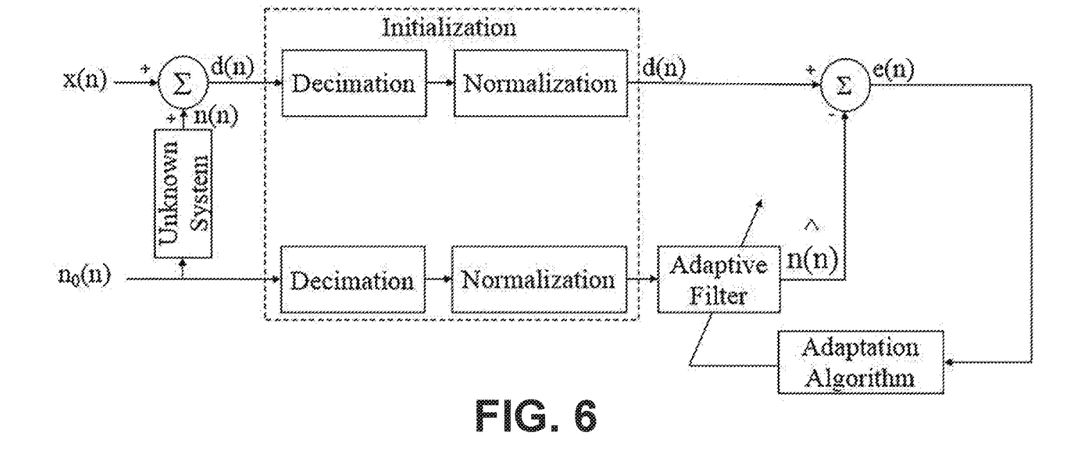
FIG. 6 is a block diagram of an embodiment of an adaptive noise cancellation algorithm.

Adaptive noise cancellation is another noise cancellation technique that can be used to remove the acoustic noise interference. FIG. 6 is block diagram of an adaptive noise cancellation subtraction algorithm that is suitable for this purpose. In order to determine the best noise cancellation technique, performance of least mean squares (LMS), sign LMS, normalized LMS, and fast-block LMS adaptive noise cancellation algorithms were compared with the spectral subtraction noise cancellation algorithm in the aforementioned study.

The algorithm illustrated in FIG. 6 is similar to the case that was considered for spectral subtraction based noise cancellation, i.e., one in which the noisy measurement d(n) acquired in the data channel is a result of superimposition of desired signal x(n) and a manifestation of reference acoustic noise n(n) as shown in Equation 1. It is assumed that the desired signal x(n) is statistically independent of n(n) and $n_0(n)$, i.e., that n(n) and n0(n) are correlated in some sense. In adaptive noise cancellation algorithm, both d(n) and $n_0(n)$ were passed through an initialization block that decimated the signals from 10 kHz to 1 kHz and then normalized in amplitude. The normalized noise $n_0(n)$ is filtered to produce $\hat{n}(n)$, an estimate of n(n) in minimum mean squared sense. Equations 4, 5, and 6 represent the filtering, error computation, and weight update operations of LMS-based adaptive noise cancellation algorithm.

$$\hat{n}(n) = w^T(n) * n_0(n) \quad \text{(Equation 4)}$$

$$e(n) = d(n) - \hat{n}(n) \quad \text{(Equation 5)}$$

$$w(n+1) = w(n) + \mu x(n) e(n) \quad \text{(Equation 6)}$$

In Equation 4, (n) represents the computed coefficients of the adaptive filter based on the order (M), $\mu$ provides the step size for the weight update operation, e is the computed error which is considered to be the noise free estimate $\hat{x}(n)$, and n is the sample index. In the study, M was set to 300 and $\mu$ was set to 0.01 for LMS. Sign LMS and normalized LMS were implemented using Equations (7) and (8), respectively.

$$w(n+1) = w(n) + \mu \text{sign}(x(n)) e(n) \quad \text{(Equation 7)}$$

$$w(n+1) = w(n) + \frac{\mu^2}{\Delta + \sigma^2_{n_0(n)}} x(n) e(n) \quad \text{(Equation 8)}$$

In Equation 7, sign represents a standard signum function and, in Equation 8, $\Delta$ is a constant and $\sigma$ is the standard deviation of $n_0(n)$ and this parameter depends on the order of the filter. For sign LMS, M was set to 300 and $\mu$ was set to 0.01. For normalized LMS, M was set to 300, $\mu$ was set to 0.3, and $\Delta$ was set to 0.1. The block LMS was implemented using a fast Fourier transform based algorithm. The $\mu$ was set to 0.5, the block size and M were set to 300, and the forgetting factor ($\gamma$) and initial average power estimate (P) were set to 0.1.

In order to assess the performance of the tested noise cancellation techniques, evaluation metrics based on the estimated average noise figure (NF) and SNR were computed after application of each noise cancellation technique. The average NF is estimated between the corresponding variances ($\sigma^2$) of d(n) and $\hat{x}(n)$; prior computing the average NF and SNR, an estimate of the noise $\hat{n}(n)$ is computed by subtracting $\hat{x}(n)$ resulting from a specific noise cancellation algorithm and the noisy measurement d(n). Then, the SNR is estimated between the corresponding variances ($\sigma^2$) of noise free estimate (n) and (n). It should be noted that, d(n), $\hat{x}(n)$, and $\hat{n}(n)$ were segmented into 2 second long frames with 80% overlap, with frame index (i), number of frames (v), and frame length (l) before estimating the average NF and SNR. Equations 9 and 10 present the functions that was used to estimate the average NF and SNR.

$$NF = \frac{1}{v} \sum_{i=1}^{v} 10 \log \left[ \frac{\sigma|^2 d_i(n)|}{\sigma|^2 \hat{x}_i(n)|} \right] \quad \text{(Equation 9)}$$

$$SNR = \frac{1}{v} \sum_{i=1}^{v} 10 \log \left| \frac{\sigma|^2 \hat{x}_i(n)|}{\sigma|^2 \hat{n}_i(n)|} \right| \quad \text{(Equation 10)}$$

Table 2 shows the estimated average NFs and SNRs of spectral subtraction, LMS, sign LMS, normalized LMS, and fast-block LMS algorithms respectively. A lower value of the estimated NF and a higher value of estimated SNR is indicative of greater proportion of noise being removed. Accordingly, the algorithm that provides the lowest value of NF and the highest value of SNR is considered to perform best.

TABLE 2

Estimated Average NFs and SNRs

| Noise Cancellation | NF(dB) | SNR(dB) |
|---|---|---|
| Spectral Subtraction | 20.54 | −8.16 |
| LMS | 25.43 | −9.75 |
| Sign LMS | 22.46 | −8.48 |
| Normalized LMS | 25.12 | −9.76 |
| Fast Block LMS | 25.38 | −9.20 |

Figure 7A:
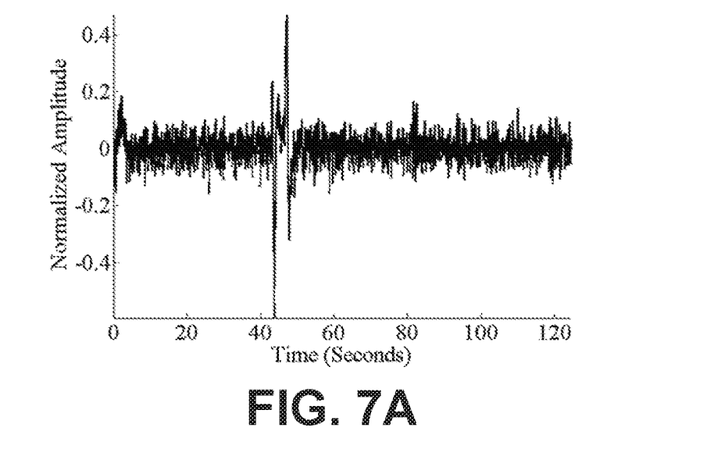
FIG. 7A is a graph that shows an example measured blood flow acoustic pressure signal.
Figure 7B:
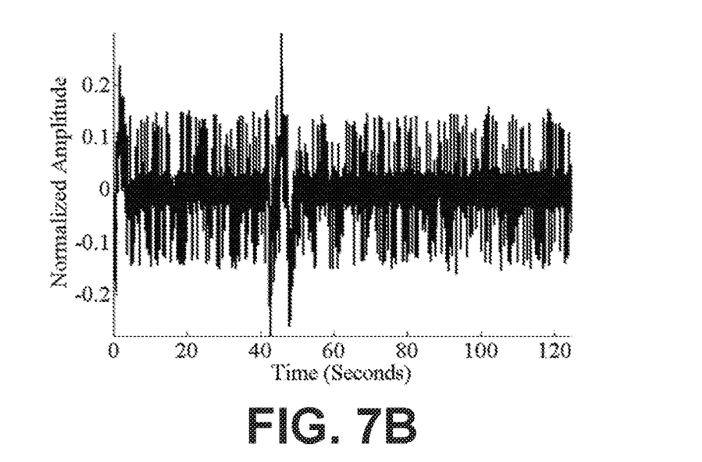
FIGS. 7B-7F are graphs that show examples of signal-to-noise ratio (SNR)-enhanced acoustic pressure signals obtained using (B) spectral subtraction, (C) LMS-based adaptive noise cancellation, (D) sign LMS-based adaptive noise cancellation, (E) normalized LMS-based adaptive noise cancellation, and (F) block LMS-based adaptive noise cancellation.
Figure 7C:
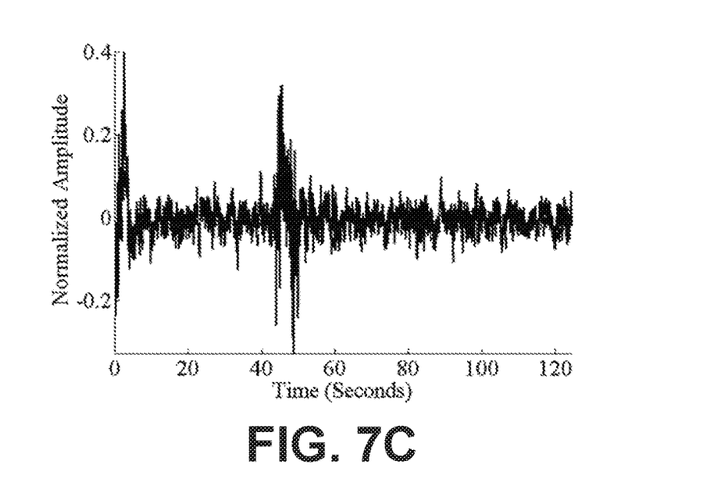
Figure 7D:
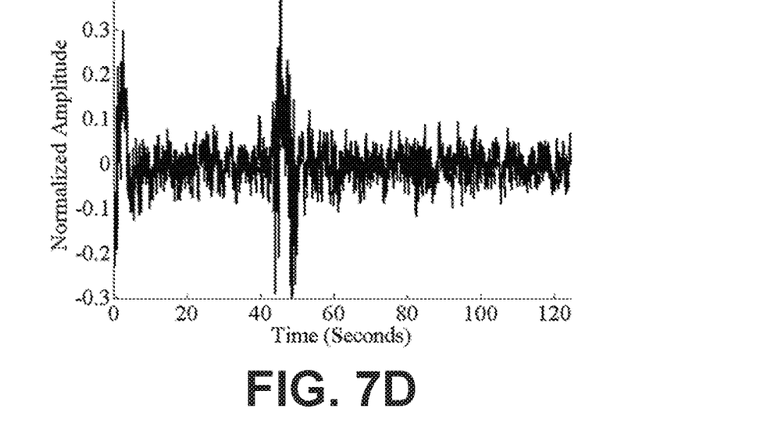
Figure 7E:
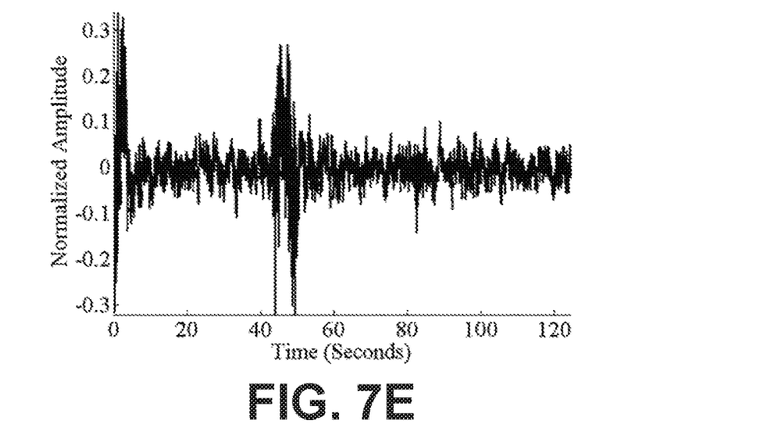
Figure 7F:
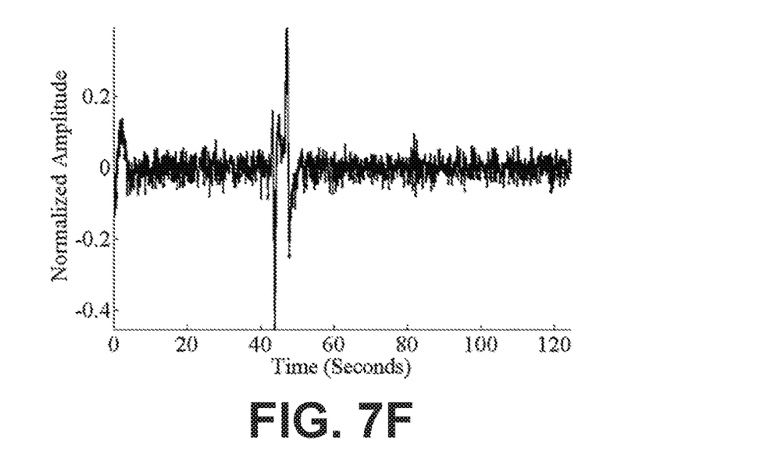

After application of spectral subtraction, $P_{total}$ shows an average estimated SNR of −8.16 dB. Spectral subtraction also provided considerable attenuation to the artifacts (see FIG. 7B; noisy measured signal shown in FIG. 7A). On the other hand, the average estimated SNR of $P_{total}$ after adaptive noise cancellation based on LMS and sign LMS were found to be −9.75 and −8.48 dBs, respectively. FIGS. 7C and 7D show the resultant outputs of LMS and sign LMS. With respect to normalized LMS and fast-block LMS, the post noise cancellation average estimated SNRs were found to be −9.76 and −9.20 dBs, respectively. The normalized LMS and fast-block LMS have not provided considerable artifact attenuation in comparison to other noise cancellation techniques (see FIGS. 7e and 7f).

Though sign LMS quantitatively provides almost similar performance to that of spectral subtraction, spectral subtraction outperformed the sign LMS in attenuating the artifacts and providing better estimates of NF and SNR, especially in the periods of d(n) where the artifact is not present. Thus, it was concluded spectral subtraction provides better performance in estimating x(n) from d(n) as compared to LMS, sign LMS, normalized LMS, and fast-block LMS adaptive noise cancellation algorithms.

Once noise cancellation has been performed source separation can be performed on the SNR-enhanced acoustic pressure signal (i.e., SNR-enhanced $P_{dynamic}$) to extract the acoustic heart and respiratory signals. In some embodiments, the source separation comprises wavelet-based source separation. Accordingly, with reference to block 64 of FIG. 4, discrete wavelet decomposition can be performed on the SNR-enhanced acoustic pressure signal to obtain biological signals, such as heart and respiratory signals. In particular, wavelet-based MRA is implemented in order to unmask the underlying biological signals. In MRA, the given signal $\hat{x}(n)$, i.e., the SNR-enhanced $P_{dynamic}$, is decomposed into various levels of approximation (A) and detail (D) coefficients according to Equation 11.

$$A_m(n) = <\hat{x}(n), \varphi_{mk}(n)>$$

$$D_m(n) = <\hat{x}(n), \psi_{mk}(n)> \quad \text{(Equation 11)}$$

where the < > operator represents inner product, m represents the decomposition level, k represents the translation, ψ represents the mother wavelet with R vanishing moments, and φ corresponds to its scaling function. In order to obtain the approximations and details of the subsequent levels, the wavelet (ψ) and scaling (φ) functions are represented as recursive functions given in Equation 12.

$$\psi(n) = \sum_{p=-\infty}^{\infty} h(p)\varphi(2n - p) \quad \text{(Equation 12)}$$

$$\varphi(n) = \sum_{p=-\infty}^{\infty} g(p)\varphi(2n - p)$$

In Equation 12, h(p) and g(p) are impulse responses of low pass and high pass quadrature mirror filters, respectively. The approximation and detail coefficients at each level are a result of convolution between the signal (n) with the impulse responses of h(p) and g(p). The approximation coefficients obtained at each level are down sampled by a factor of two and decomposed further into finer approximations and details. This process is continued until all the levels of the MRA are reached. After all the approximation and detail coefficients are obtained from the MRA, level-based hard thresholding is performed (block 66) by setting the coefficients corresponding to all the scales to zero expect for the coefficients of the interest in a particular level. Using this hard thresholding process, the biological signals can be extracted in the wavelet domain.

After application of the hard thresholding, the new coefficients are reconstructed back into the time domain to extract the various signals that make up the SNR-enhanced acoustic pressure signal, as indicated in block 68. Both the acoustic heart and respiratory signals exhibit a different behavior in the wavelet domain in the sense that the acoustic heart signals are highly dynamic, non-stationary and acoustic respiratory signals are relatively slow varying. Therefore, the chosen mother wavelet (ψ) should provide a reasonably good low and high frequency resolution to the underlying biological signals of (n) through compact support. In the study, the lower cutoff frequency of the pressure field microphone 28 was set to 3.15 Hz. Therefore, any underlying biological signals of interest that contained frequency components below 3.15 Hz would have been attenuated and appeared as discontinuities in the measured pressure data. As a result, the chosen ψ needs to be able to detect the presence of hidden discontinuities. Finally, the ψ should be orthogonal to avoid phase distortions from the transformation. All the requirements of the study were satisfied by the Coiflet wavelet with four vanishing moments. As shown in block 70, if monitoring is to be continued, flow returns to block 60.

Figure 8A:
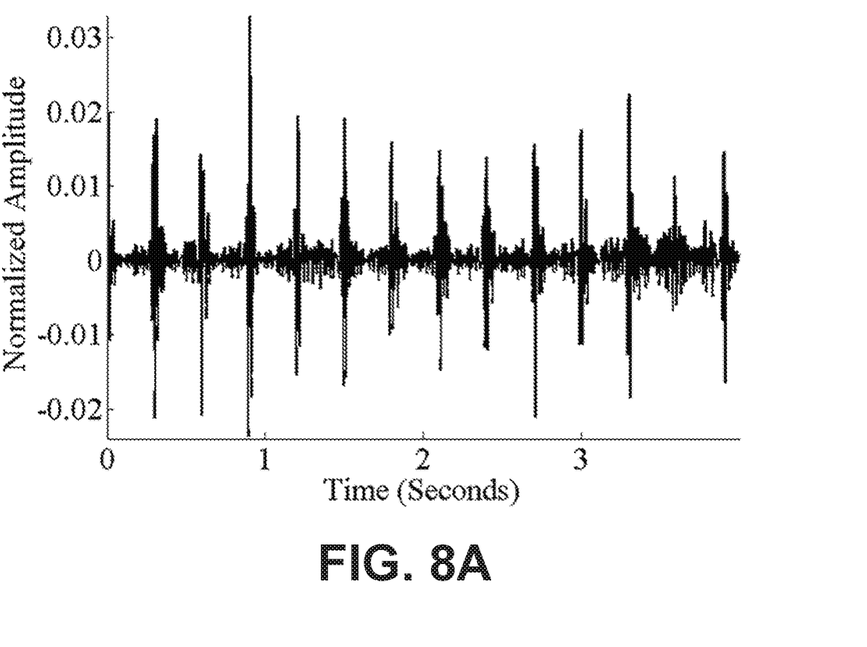
FIG. 8A is a graph that shows an example of an acoustic heart signal extracted from an SNR-enhanced acoustic pressure signal.
Figure 8B:
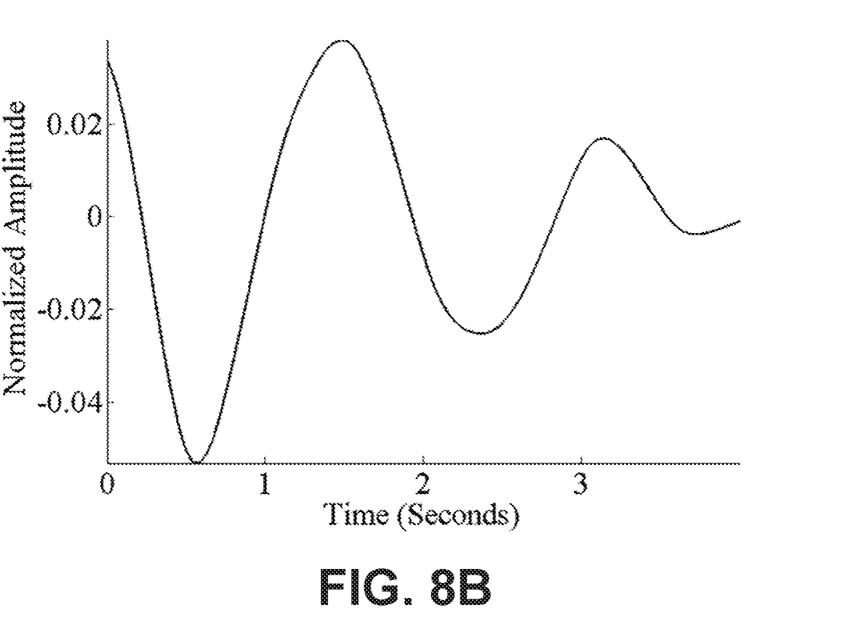
FIG. 8B is a graph that shows an example of an acoustic respiratory signal extracted from an SNR-enhanced acoustic pressure signal.

During the study, the estimate (n) obtained from spectral subtraction was subjected to MRA using fourth-order Coiflet wavelet. The level of decomposition at which the detail coefficients were retained was biological signal-dependent and thus, for acoustic heart signals, the coefficients of interest were identified at level four and, for acoustic respiratory signals, the coefficients of interest were identified at level ten. Following the ten-level MRA decomposition, coefficients of interest in a particular level were retained and a hard threshold was applied to coefficients corresponding to other scales. The acoustic heart and respiratory pulses masked in (n) were extracted by performing a hard threshold on MRA coefficients, simultaneously retaining details coefficients of level four (D4), level ten (D10) and reconstructing them individually back into time domain. FIGS. 8A and 8B show the extracted acoustic heart and respiratory pulses obtained after reconstruction.

The acoustic heart signals were benchmarked by computing average heart rate in beats per minute (bpm) and comparing it to the average of heart rate that was recorded prior and post acquisition of the noisy measurement. Since the acoustic respiratory pulse is a slowly varying waveform, further analysis was performed on a relatively large time period. A first-order sample difference was computed in order to identify the presence of any discontinuities that may have been present due to the bandlimited frequency response of the pressure field microphone 28. The corresponding results are shown in FIG. 9.

Figure 9:
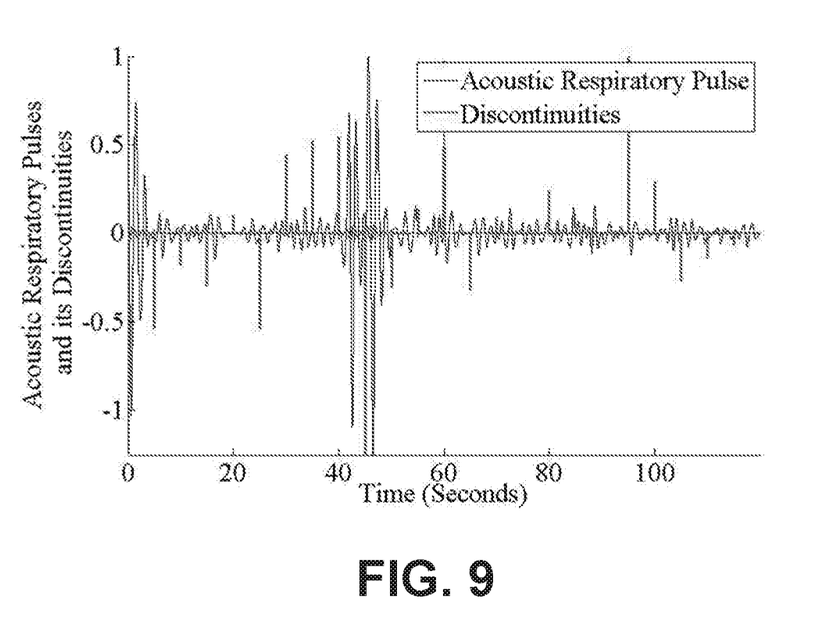
FIG. 9 is a graph that shows an example acoustic respiratory signal and corresponding discontinuities.

From FIG. 9, it was observed that the slow moving respiratory signal was attenuated and discontinuities were introduced due to this attenuation. The number of discontinuities present were in direct correlation to the average respiratory rate in breaths per minute (rpm) acquired prior and post the d(n) acquisition for the purpose of benchmarking. The discontinuities can also be identified using MRA. The extracted acoustic respiratory pulse was decomposed into first of level approximation and detail coefficients using fifth order Coiflet wavelet to obtain similar results.

Table 3 presents error analysis results of computed heart and respiratory rates benchmarked with modalities obtained using conventional devices for all the venous and arterial blood flow dynamics given in Table 1. The error percentage computed by benchmarking with conventionally measured modalities validate the extracted acoustic heart and respiratory signals. From Table 3, it was observed that the system 10 measures the heart rate with an estimated error less than 4%, i.e., with higher precision when compared to the existing heart rate monitors. With respect to the respiratory rate, the system 10 recorded a highest estimation error of 1.5 rpm, which can be regarded as a precise measurement in comparison to an optimized respiratory rate monitor.

TABLE 3

Error Analysis Results of Heart and Respiratory Rate Benchmarking

| | Heart Rate (bpm) | | | Respiratory Rate (rpm) | | |
|---|---|---|---|---|---|---|
| Index | Recorded Value | Computed Value | Error (± %) | Recorded Value | Computed Value | Error (± %) |
| 1a | 95 | 99 | 3.78 | 10 | 10.5 | 5 |
| 5a | 110.5 | 102 | | 10 | 10 | |
| 6a | 128 | 120 | | 10 | 11 | |
| 1b | 218 | 210 | 0.59 | 10 | 11.5 | 15 |
| 5b | 216.5 | 217.5 | | 10 | 11.5 | |
| 6b | 222 | 225 | | 10 | 11.5 | |
| 2b | 108.5 | 105 | 1.87 | 10 | 11 | 13 |
| 3a | 116 | 112.5 | | 10 | 11.5 | |
| 4b | 96.5 | 97.5 | | 10 | 11.5 | |
| 2a | 179 | 180 | 2.38 | 10 | 10 | 5 |
| 3b | 200 | 195 | | 10 | 11 | |
| 4a | 204.5 | 194.6 | | 10 | 10.5 | |

Continuous Blood Pressure Extraction

As noted above in relation to FIG. 3, continuous blood pressure can also be extracted from the measured acoustic pressure signal, $P_{total}$ using a further signal processing framework. Such a process is depicted in FIG. 10, which may be described as illustrating a method for extracting continuous blood pressure from a measured acoustic pressure signal.

Figure 10:
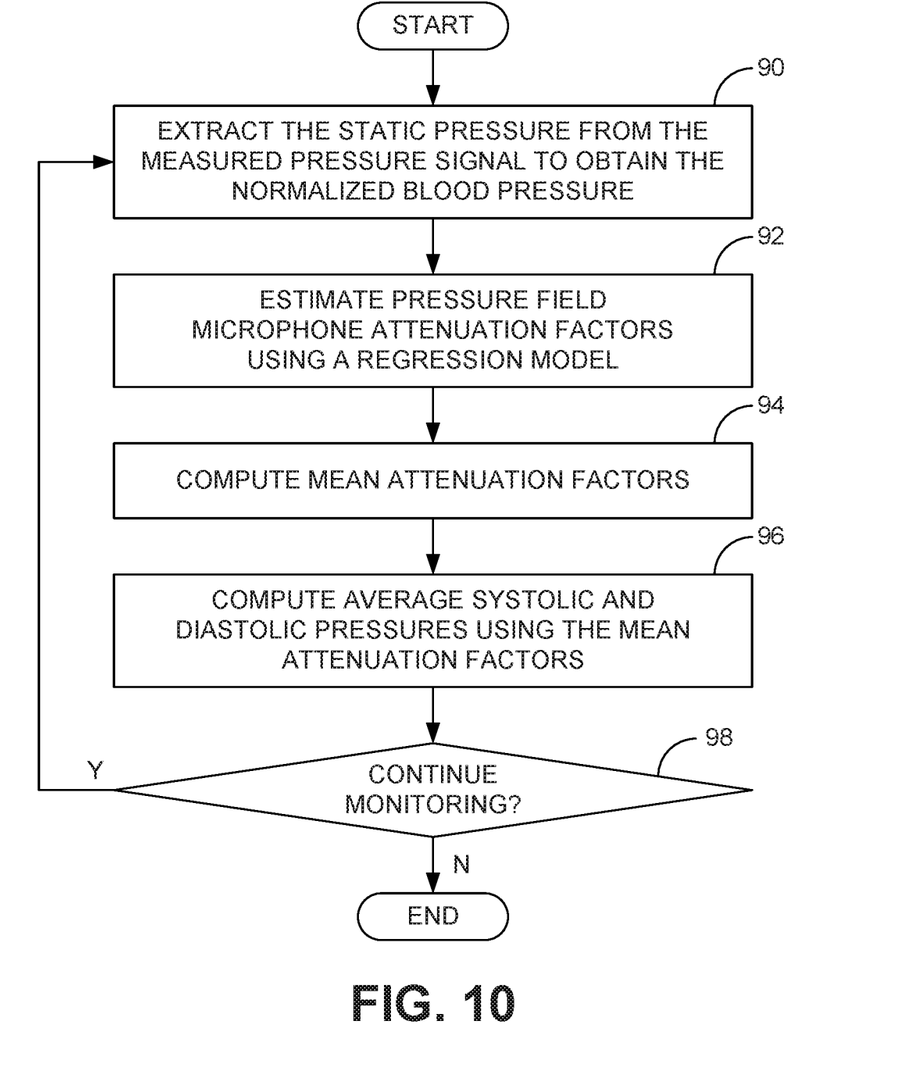
FIG. 10 is a flow diagram of an embodiment of a method for extracting continuous blood pressure from a measured blood flow pressure signal.

Beginning with block 90 of FIG. 10, the static pressure, $P_{static}$, is extracted from the measured acoustic pressure signal, now to obtain the normalized blood pressure. As noted above, even though $P_{static}$ is equalized in the system 10, now includes traces of $P_{static}$. This is due to an insufficient discharge time constant of the pressure field microphone 28. Making use of this limitation, $P_{static}$, which is the normalized blood pressure, can be extracted by computing a local mean for every 25 ms from the measured $P_{total}$. This local mean computation segments $P_{total}$ and, in effect, compresses the number of data samples of $P_{total}$ from 10,000 samples to 40 samples for each second. The segment length for mean computation was deliberately chosen to be 25 ms because all the harmonics of blood acoustic pressure signal are present between 0 to 20 Hz. Extraction of $P_{static}$ from $P_{total}$ provides the normalized blood pressure. During the study, the computed normalized blood pressure was validated by establishing comparison between the human and animal blood pressure data. This comparison was accomplished by estimating the magnitude squared coherence between the normalized blood pressure data derived from recording index 1a and the Physionet arterial blood pressure derived from a multi-parameter waveform database using Welch's overlapped segment averaging.

It is not possible to directly estimate the systolic and diastolic pressure from the extracted normalized blood pressure. To estimate those pressures, pressure field microphone attenuation factors $k_1$, $k_2$, which correspond to systolic and diastolic pressures, respectively, are first estimated using a regression model, as shown in block 92. As indicated in Equation 13 below, sys is the systolic pressure, dia is the diastolic pressure, M is the mean arterial pressure obtained using the conventional devices, P is the local maxima, and V is the local minima of the normalized blood pressure obtained after compression of $P_{total}$. As noted above, $k_1$ and $k_2$ are the sensor attenuation factors corresponding to the systolic and the diastolic pressures, respectively.

$$sys = k_1 \cdot (P+M)$$

$$dia = k_2 \cdot (V+M) \qquad \text{(Equation 13)}$$

The regression model first estimates the systolic and diastolic attenuation factors using the blood pressure data obtained from conventional instruments, i.e., M, sys, and dia. The systolic and diastolic pressures can then be estimated using the computed regression model. The sensor attenuation factors k1 and k2 can be computed using the normalized blood pressure data for recording indices 1a to 6b. During the study, the factors k1 and k2 were computed to be 1.1078±0.0658 and 0.8854±0.0449, respectively. Once the factors are computed, the mean values of the obtained $k_1$ and $k_2$ can be computed (block 94) and then used to compute average systolic and diastolic pressures (block 96) using Equation 14 for all the recording indices from 1a to 6b as shown in Table 4.

TABLE 4

Error Analysis Results of Systolic and Diastolic Pressures Benchmarking

| | Systolic Pressure (mmHg) | | | Diastolic Pressure (mmHg) | | |
|---|---|---|---|---|---|---|
| Index | Recorded Value | Computed Value | Error (± %) | Recorded Value | Computed Value | Error (± %) |
| 1a | 84.5 | 82.5 | 3 | 63 | 65.96 | 1.5 |
| 5a | 45 | 41 | | 31.5 | 32.6 | |
| 6a | 39 | 39.9 | | 34 | 31.9 | |
| 1b | 189.5 | 196.6 | 5 | 152.5 | 157.2 | 1.9 |
| 5b | 181 | 187.8 | | 152.5 | 150.1 | |
| 6b | 141 | 152.9 | | 133 | 122.2 | |
| 2b | 52.5 | 49.9 | 5.6 | 39 | 39.8 | 4.2 |
| 3a | 44.5 | 42.1 | | 30.5 | 33.6 | |
| 4b | 51 | 47.6 | | 37.5 | 38.1 | |
| 2a | 124 | 135.7 | 4.1 | 110 | 108.5 | 2.4 |
| 3b | 171.5 | 175.6 | | 143 | 140.3 | |
| 4a | 186.5 | 190.5 | | 158 | 152.3 | |

From Table 4, it was observed that the system 10 is able to predict systolic pressures with an estimated average error rate less than 6% and diastolic pressures with an estimated average error rate less than 5% in comparison to the current gold standard.

As shown in block 98, if monitoring is to be continued, flow returns to block 90.

Alternative Embodiments

Figure 11:
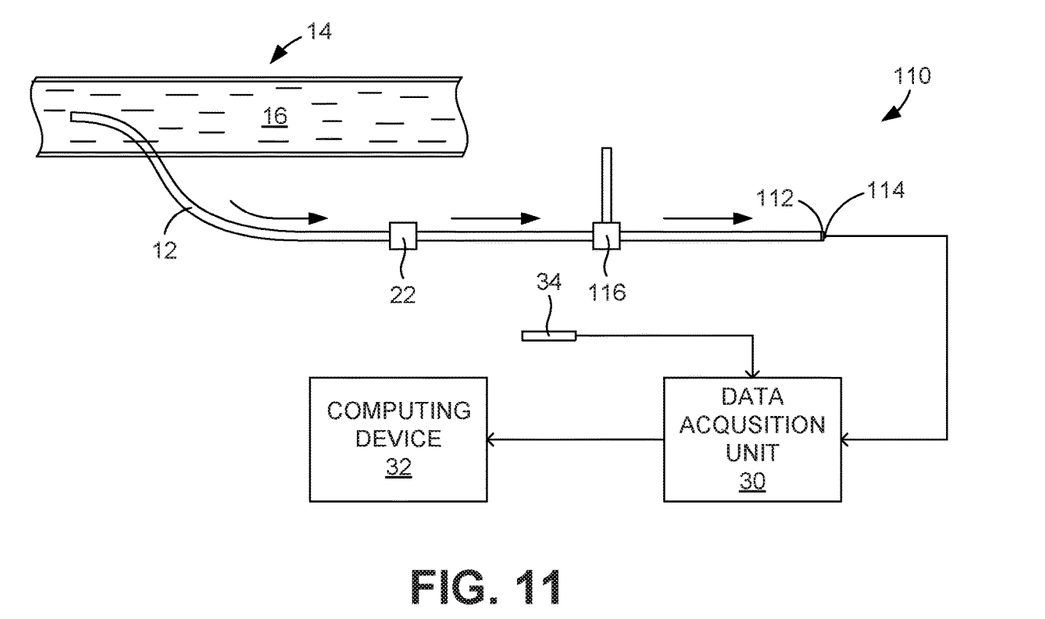
FIG. 11 is a schematic diagram of an alternative embodiment of a system for determining multiple physiological parameters from blood flow dynamics.

In the above disclosure, the continuous blood pressure was determined by processing the acoustic pressure signal, $P_{total}$, measured by the pressure field microphone. In other embodiments, the system can be configured to directly measure the blood pressure. FIG. 11 illustrates an example of such an embodiment. In particular, FIG. 11 shows a system 110 that is similar in many ways to the system 10 shown in FIG. 1. Accordingly, the system 110 includes a catheter 12 that is configured for insertion in a subject's blood vessel 14. In this embodiment, however, the system 110 does not include a coupling member and a waveguide. Instead, the proximal end of the catheter 12 is terminated by a small flexible barrier 112, which also can comprise a thin polymeric membrane. Mounted to the barrier 112 is a first microphone 114 that, like first microphone 28, can measure the field pressure of the blood flow. In some embodiments, the microphone 114 comprises a microelectromechanical system (MEMS) microphone.

As is further shown in FIG. 11, the system 110 also includes pressure sensor 116 that is mounted to the catheter 12 at a position upstream of the barrier 112. In some embodiments, the pressure sensor 116 comprises a MEMS pressure sensor contained within a housing that is placed in fluid communication with the blood inside the catheter via an opening (not shown) formed in the catheter. When such a pressure sensor 116 is provided, the systolic and diastolic pressures can be directly measured without needing to estimate them using the regression model based upon the measured acoustic pressure signal.

It is noted that other sensor can be added to the system 110 (or system 10) for the purpose of measuring other physiological parameters. For example, a pulse oximeter can be provided to measure the subject's blood oxygen saturation.

The invention claimed is:

1. A system for determining physiological parameters from blood flow dynamics, the system comprising:
   a catheter configured for insertion into a blood vessel of a subject through which blood flows;
   a flexible barrier associated with the catheter configured to oscillate in response to changes in pressure of the blood within the catheter;
   a pressure field microphone configured to measure a pressure field induced by the oscillation of the flexible barrier and to generate a measured acoustic pressure signal that can be processed to determine the physiological parameters;
   an acoustic microphone configured to measure ambient noise from the environment surrounding the subject and generate a measured acoustic signal that can be used for noise cancellation; and
   a computing device including a signal processing system configured to receive the measured acoustic pressure signal and the measured acoustic signal and determine the physiological parameters, including heart rate, respiratory rate, and continuous blood pressure.

2. The system of claim 1, wherein the flexible barrier comprises a polymeric membrane.

3. The system of claim 1, wherein the pressure field microphone comprises a condenser microphone.

4. The system of claim 1, further comprising a coupling member connected to a proximal end of the catheter and to which the flexible barrier is mounted.

5. The system of claim 4, further comprising a waveguide having an internal air chamber, the coupling member being mounted to a distal end of the waveguide and the pressure field microphone being provided within the air chamber at a proximal end of the waveguide such that the pressure field propagates through the air chamber from the flexible barrier to the pressure field microphone.

6. The system of claim 5, wherein the internal air chamber is conical and configured to focus the pressure field on the pressure field microphone.

7. The system of claim 1, wherein the pressure field microphone is mounted to the flexible barrier.

8. The system of claim 1, wherein the signal processing system is configured to perform noise cancellation on the measured acoustic pressure signal with reference to the measured acoustic signal to generate an enhanced acoustic pressure signal.

9. The system of claim 8, wherein the signal processing system implements spectral subtraction to perform the noise cancellation.

10. The system of claim 9, wherein the signal processing system is further configured to perform source separation on the enhanced acoustic pressure signal to extract a heart signal from which heart rate can be determined and a respiratory signal from which respiratory rate can be determined.

11. The system of claim 10, wherein the signal processing system performs wavelet-based source separation to extract the heart and respiratory signals.

12. The system of claim 1, wherein the signal processing system is configured to extract a static pressure signal from the measured acoustic pressure signal and to compute average systolic and diastolic blood pressures from the static pressure signal using a regression model.

13. The system of claim 12, wherein the signal processing system computes attenuation factors using the regression model, the attenuation factors corresponding to systolic and diastolic blood pressures.

14. The system of claim 1, further comprising a pressure sensor mounted to the catheter configured to directly measure blood pressure.

15. A method for determining physiological parameters from blood flow dynamics, the method comprising:
   inserting a catheter into a blood vessel of a subject through which blood flows;
   associating with the catheter a flexible barrier configured to oscillate in response to changes in pressure of the blood within the catheter;
   measuring a pressure field of the blood flow induced by the oscillation of the flexible barrier using a pressure field microphone to generate a measured acoustic pressure signal that can be processed to determine the physiological parameters;
   measuring ambient noise from the environment surrounding the subject using an acoustic microphone to generate a measured acoustic signal that can be used for noise cancellation;
   operating a computing device including a signal processing system to perform noise cancellation on the measured acoustic pressure signal using the measured acoustic signal to obtain an enhanced acoustic pressure signal; and
   operating the computing device to process the enhanced acoustic pressure signal to obtain a heart signal and a respiratory signal and determine the physiological parameters, including heart rate, respiratory rate, and continuous blood pressure.

16. The method of claim 15, wherein processing the enhanced acoustic pressure signal comprises performing source separation on the enhanced acoustic pressure signal to extract the heart signal and the respiratory signal.

17. The method of claim 15, further comprising processing the measured acoustic pressure signal using a regression model to obtain continuous blood pressure.

* * * * *